United States Patent
Morishita et al.

(10) Patent No.: US 10,052,268 B2
(45) Date of Patent: Aug. 21, 2018

(54) OXIDATIVE HAIR DYE COMPOSITION

(71) Applicant: HOYU CO., LTD., Nagoya-shi, Aichi-ken (JP)

(72) Inventors: Nana Morishita, Aichi-ken (JP); Hiroki Takahashi, Aichi-ken (JP); Mai Nagatoshi, Aichi-ken (JP)

(73) Assignee: HOYU CO., LTD., Nagoya-shi (JP)

( * ) Notice: Subject to any disclaimer, the term of this patent is extended or adjusted under 35 U.S.C. 154(b) by 0 days.

(21) Appl. No.: 15/602,272

(22) Filed: May 23, 2017

(65) Prior Publication Data

US 2017/0340524 A1 Nov. 30, 2017

(30) Foreign Application Priority Data

May 25, 2016 (JP) ................................. 2016-103913

(51) Int. Cl.
| | | |
|---|---|---|
| *A61Q 5/10* | (2006.01) | |
| *A61K 8/02* | (2006.01) | |
| *A61K 8/73* | (2006.01) | |
| *A61Q 5/08* | (2006.01) | |
| *A61K 8/34* | (2006.01) | |
| *A61K 8/39* | (2006.01) | |
| *A61K 8/41* | (2006.01) | |
| *A61K 8/86* | (2006.01) | |

(52) U.S. Cl.
CPC ............ *A61K 8/0216* (2013.01); *A61K 8/347* (2013.01); *A61K 8/39* (2013.01); *A61K 8/411* (2013.01); *A61K 8/731* (2013.01); *A61K 8/86* (2013.01); *A61Q 5/08* (2013.01); *A61Q 5/10* (2013.01); *A61K 2800/43* (2013.01); *A61K 2800/882* (2013.01)

(58) Field of Classification Search
CPC .... A61Q 5/10; A61K 8/731; A61K 2201/922; A61K 2800/43; A61K 2800/882
See application file for complete search history.

(56) References Cited

U.S. PATENT DOCUMENTS

| | | | | |
|---|---|---|---|---|
| 6,312,677 | B1 * | 11/2001 | Millequant | ............... A61K 8/39 424/401 |
| 2007/0157399 | A1 * | 7/2007 | Nobuto | .................... A61K 8/44 8/405 |

FOREIGN PATENT DOCUMENTS

JP 2013-151464 A 8/2013

* cited by examiner

*Primary Examiner* — Eisa B Elhilo
(74) *Attorney, Agent, or Firm* — Posz Law Group, PLC

(57) ABSTRACT

An oxidative hair dye composition contains a first agent that includes an alkaline agent and is a cream formulation and a second agent that includes an oxidant and is liquid. The oxidative hair dye composition at the time of use has a viscosity at 25° C. of 3,000 to 10,000 mPa·s. The oxidative hair dye composition further includes (A) a salt of an oxidative dye, (B) a cationic surfactant in a content of 0.15% by mass or more, (C) a nonionic surfactant having an HLB value of 17 to 20, and (D) a nonionic surfactant having an HLB value of 11 or less.

5 Claims, No Drawings

OXIDATIVE HAIR DYE COMPOSITION

BACKGROUND OF THE INVENTION

The present invention relates to an oxidative hair dye composition including as a dye a salt of an oxidative dye.

In general, as a hair cosmetic composition, there has been known a hair dye exhibiting effects by mixing a plurality of chemicals. As such a hair cosmetic composition, for example, there has been known an oxidative hair dye composed of a first agent containing an alkaline agent and an oxidative dye, and a second agent containing an oxidant such as hydrogen peroxide. The alkaline agent promotes the action of the oxidant contained in the second agent, and also improves the hair-dyeing power by swelling hair so as to improve the permeability of the dye into the hair. The oxidative dye is a compound capable of developing a color due to the oxidation polymerization caused by the oxidant contained in the second agent, and is classified into a dye intermediate and a coupler. For example, the oxidative hair dye disclosed in Japanese Laid-Open Patent Publication No. 2013-151464 includes a first agent that is a cream formulation containing an oxidative dye that is an acid addition salt.

SUMMARY OF THE INVENTION

When an oxidative dye that is an acid addition salt is used, there is a problem that the viscosity of the composition is decreased. On the other hand, when a first agent of a cream formulation having a relatively high viscosity is used, the miscibility at the time of use may be degraded. In particular, when the oxidative hair dye is composed of a first agent that is a cream formulation and a second agent that is liquid, there is a problem that the miscibility is degraded.

An objective of the present invention is to provide an oxidative hair dye composition that is composed of a plurality of agents, uses an oxidative dye of an acid addition salt, and improves the miscibility while achieving a desired viscosity.

The present invention is based on the finding that in an oxidative hair dye composition composed of a plurality of agents and using an oxidative dye of an acid addition salt, the use of a predetermined surfactant in combination improves the miscibility while achieving a desired viscosity. The numerical values representing the contents of the components in terms of percent by mass are the numerical values in a formulation inclusive of a solubilizer such as water.

To achieve the foregoing objective and in accordance with one aspect of the present invention, an oxidative hair dye composition is provided that comprises a first agent that includes an alkaline agent and is a cream formulation and a second agent that includes an oxidant and is liquid. The oxidative hair dye composition at the time of use has a viscosity at 25° C. of 3,000 to 10,000 mPa·s. The oxidative hair dye composition further comprises (A) a salt of an oxidative dye, (B) a cationic surfactant in a content of 0.15% by mass or more, (C) a nonionic surfactant having an HLB value of 17 to 20, and (D) a nonionic surfactant having an HLB value of 11 or less.

The (B) component may have an alkyl group having 20 or more carbon atoms. The mass ratio of the content of the (D) component to the content of the (C) component may be 0.1 to 2. The oxidative hair dye composition may further comprise (E) a hydroxyalkyl cellulose or a derivative thereof. The first agent and the second agent may be shaken and mixed with each other in an airtight container at the time of use, and the filling ratio of the mixture of the first agent and the second agent in the airtight container may be 20 to 80% by volume.

Other aspects and advantages of the present invention will become apparent from the following detailed description illustrating by way of example the principles of the present invention.

DETAILED DESCRIPTION OF THE PREFERRED EMBODIMENTS

Hereinafter, an oxidative hair dye composition according to one embodiment of the present invention will be described. A two-part type oxidative hair dye composition is composed of a first agent and a second agent, and after the first agent and the second agent are mixed with each other, the two-part type oxidative hair dye composition is used for dyeing hair. Alternatively, the oxidative hair dye composition may also be constituted as a three-part type oxidative hair dye composition.

<Two-Part Type Oxidative Hair Dye Composition>

The two-part type oxidative hair dye composition is composed of, for example, a first agent containing an alkaline agent and an oxidative dye, and a second agent containing an oxidant and the like.

(First Agent of Two-Part Type Oxidative Hair Dye Composition)

The first agent contains, in addition to the alkaline agent and the oxidative dye, for example, (B) a cationic surfactant, (C) a nonionic surfactant having an HLB value of 17 to 20, (D) a nonionic surfactant having an HLB value of 11 or less, and (E) a hydroxyalkyl cellulose or a derivative thereof. The oxidative dye is a compound capable of developing a color due to the oxidation polymerization caused by the oxidant contained in the second agent, and is classified into a dye intermediate and a coupler. In the present embodiment, as the oxidative dye, (A) a salt of an oxidative dye that is an acid addition salt is used. Examples of the acid addition salt include an organic acid addition salt and an inorganic acid addition salt. More specifically, examples of the acid addition salt include a hydrochloride, a sulfate, a hydrobromide, a citrate, a succinate, a tartarate, a lactate, a tosylate, a benzenesulfonate, a phosphate, an acetate, a malate, a benzoate, and a salicylate. Only one of these specific examples may be contained alone, or two or more of these specific examples may be contained in combination. Among these, from the viewpoint of being excellent in hair-dyeing power, a hydrochloride and a sulfate are preferable.

Specific examples of the dye intermediate include salts of p-phenylenediamine, toluene-2,5-diamine (p-toluylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chloro-p-phenylenediamine, 4-amino-m-cresol, 2-amino-4-hydroxy ethyl aminoanisole, and 2,4-diaminophenol. Only one of these specific examples of the dye intermediate may be contained alone, or two or more of these specific examples of the dye intermediate may be contained in combination.

The coupler develops a color by bonding to the dye intermediate. Specific examples of the coupler include salts of resorcin, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, and 1,5-dihydroxynaphthalene. Only one of these specific examples of the coupler may be contained alone, or two or more of these specific examples of the coupler may be contained in combination. The (A) component is preferably composed of at least one selected from the specific examples of the dye intermediate and at least one selected from the specific examples of the coupler from the viewpoint of providing variations of hair color tone. The first agent may optionally contain, as the dyes other than the aforementioned oxidative dyes, for example, the oxidative dyes not in the form of salts, the oxidative dyes listed in "The Japanese Standards of Quasi-Drug Ingredients" (published by Yakuji Nippo Ltd., June 2006).

The lower limit of the content of the (A) component in the oxidative hair dye composition, namely, the mixture of the first agent and the second agent, is appropriately set, and is preferably 0.1% by mass or more, more preferably 0.5% by mass or more, furthermore preferably 1% by mass or more. When the content of the (A) component is 0.1% by mass or more, the hair-dyeing power among other things is more improved.

The upper limit of the content of the (A) component in the mixture of the first agent and the second agent is appropriately set, and is preferably 10% by mass or less, more preferably 7% by mass or less, and furthermore preferably 5% by mass or less. When the content of the (A) component is 10% by mass or less, the decrease of the viscosity of the mixture is suppressed.

The lower limit of the content of the (A) component in the first agent is appropriately set, and is preferably 0.1% by mass or more, more preferably 0.5% by mass or more, and furthermore preferably 1% by mass or more. When the content of the (A) component is 0.1% by mass or more, the hair-dyeing power among other things is more improved. The upper limit of the content of the (A) component in the first agent is appropriately set, and is preferably 20% by mass or less, more preferably 14% by mass or less, and furthermore preferably 10% by mass or less. When the content of the (A) component is 20% by mass or less, the stability of the first agent is improved.

(B) The cationic surfactant imparts a desired viscosity to the mixture of the first agent and the second agent. (B) The cationic surfactant also improves the stability of the first agent containing the (A) component. Accordingly, (B) the cationic surfactant is preferably mixed in the first agent containing the (A) component. Specific examples of (B) the cationic surfactant include lauryl trimethyl ammonium chloride, cetyl trimethyl ammonium chloride, stearyl trimethyl ammonium chloride, alkyl trimethyl ammonium chloride, distearyl dimethyl ammonium chloride, cetyl trimethyl ammonium bromide, stearyl trimethyl ammonium bromide, ethyl lanolin fatty acid aminopropyl ethyl dimethyl ammonium ethyl sulfate, stearyl trimethyl ammonium saccharin, cetyl trimethyl ammonium saccharin, methacryloyloxy ethyl trimethyl ammonium chloride, behenyl trimethyl ammonium methyl sulfate, and an alkyl amide amine type cationic surfactant. Specific examples of the alkyl trimethyl ammonium chloride include behenyl trimethyl ammonium chloride, and arachidyl trimethyl ammonium chloride. Specific examples of the alkyl amide amine type cationic surfactant include: alkyloylamide ethyl diethyl amines such as diethylaminoethyl amide stearate, diethylaminoethyl amide behenate, diethylaminoethyl amide palmitate, and diethylaminoethyl amide myristate; alkyloylamide propyl dimethyl amines such as dimethyl aminopropyl amide stearate, dimethylaminopropyl amide behenate, dimethylaminopropyl amide palmitate, and dimethylaminopropyl amide myristate; alkyloylamide ethyl dimethyl amines such as dimethylaminoethyl amide stearate, dimethylaminoethyl amide behenate, dimethylaminoethyl amide palmitate, and dimethylaminoethyl amide myristate; alkyloyldimethyl amines such as behenyl dimethyl amine, and stearyl dimethyl amine; alkyloylpropyl dimethyl amines such as palmitoxypropyl dimethyl amine, and stearoxypropyl dimethyl amine; or salts thereof. Only one of these may be contained alone, or two or more of these may be contained in combination. Among these, a cationic surfactant having an alkyl group having 20 or more carbon atoms is preferable from the viewpoint of being excellent in the viscosity imparting effect to the mixture of the first agent and the second agent and being excellent in the miscibility at the time of use.

The lower limit of the content of the (B) component in the mixture of the first agent and the second agent is 0.15% by mass or more, preferably 0.2% by mass or more, and more preferably 0.4% by mass or more. When the content of the (B) component is 0.15% by mass or more, a desired viscosity is achieved. The upper limit of the content of the (B) component in the mixture of the first agent and the second agent is appropriately set, and is preferably 10% by mass or less, more preferably 5% by mass or less, and furthermore preferably 0.75% by mass or less. When the content of the (B) component is 10% by mass or less, the miscibility is more improved.

The lower limit of the content of the (B) component in the first agent is appropriately set, and is preferably 0.02% by mass or more, more preferably 0.1% by mass or more, and furthermore preferably 0.4% by mass or more. The upper limit of the content of the (B) component in the first agent is appropriately set, and is preferably 10% by mass or less, more preferably 5% by mass or less, and furthermore preferably 1.5% by mass or less. When the content of the (B) component in the first agent is specified within such a range, the stability of the first agent containing the (A) component is improved.

(C) A nonionic surfactant having an HLB value of 17 to 20 imparts a desired viscosity to the mixture of the first agent and the second agent. The (C) component is preferably a compound having a polyoxyethylene (hereinafter, referred to as "POE") chain. The number of moles of added ethylene oxide (hereinafter, referred to as "E.O.") constituting the POE chain is preferably 25 or more, more preferably 30 or more, and furthermore preferably 35 or more. In the case of a compound constituting a POE chain having a number of moles of added E.O. of 25 or more, a desired viscosity is achieved. Specific examples of the (C) component are listed as follows. It is to be noted that the numerical value in each set of the parentheses in the compound name represents the number of moles of added E.O. In the present invention, as the HLB values, the values determined from the below-described measurements are employed, and for example, the numerical values listed in the catalog published by Nikko Chemicals Co., Ltd. (2014) are listed as the reference values.

Specific examples of the (C) component include POE(25) lauryl ether (HLB: 17.1), POE(20) oleyl ether (HLB: 17), POE(50) oleyl ether (HLB: 18), POE(30) behenyl ether (HLB: 18), POE(150) behenyl ether (HLB: 19.1), POE(20) cetyl ether (HLB: 17), POE(30)cetyl ether (HLB: 19.5), POE(40) cetyl ether (HLB: 20), POE(20) stearyl ether (HLB: 18), POE(150) stearyl ether (HLB: 19.2), polyethylene glycol (45) monostearate (HLB: 18), POE(40) lanolin alcohol (HLB: 17), POE(30) phytosterol (HLB: 18), and polyethylene glycol (40) monostearate (HLB: 17.5).

HLB (hydrophile-lipophile balance), which was invented by W. C. Griffin, is a value given to a nonionic surfactant, and numerically represents the strength balance between the lipophilic group (alkyl group) and the hydrophilic group (ethylene oxide chain) of the nonionic surfactant. As the HLB value, the measured value calculated from an emulsion method is used (see "Handbook—Cosmetic/Formulation Materials—" by Nikko Chemicals Co., Ltd. (revised edition published on Feb. 1, 1977)). For the measurement of the HLB value, as a standard substance of the surfactant, sorbitan monostearate (for example, NIKKOL SS-10, HLB value: 4.7, manufactured by Nikko Chemicals Co., Ltd.) and polyoxyethylenesorbitan monostearate (for example, NIKKOL TS-10, HLB value: 14.9, manufactured by Nikko Chemicals Co., Ltd.) are used in combination. As a substance to be emulsified, liquid paraffin is used. When the liquid paraffin is possibly varied according to the type or the lot, the measurement is performed on a case-by-case basis. The liquid paraffin is emulsified with the above-described two types of surfactants, the optimal proportions of the surfactants are determined, and the required HLB value of the liquid paraffin (emulsified HLB value) is determined. The calculation expression is represented by mathematical expression (1).

[Expression 1]

HLB value of liquid paraffin=[(HLB value of polyoxyethylenesorbitan monostearate×percentage of amount used)+(HLB value of sorbitan monostearate×percentage of amount used)]/100      (1)

The required HLB value of the liquid paraffin is usually approximately 10.1 to 10.3 depending on the type and the lot. Next, the measurement of the HLB of an unknown surfactant is performed by using the liquid paraffin for which the required HLB value has been determined. When the unknown surfactant is hydrophilic, the unknown surfactant is combined with sorbitan monostearate and used to emulsify the liquid paraffin. When the unknown surfactant is hydrophobic, the unknown surfactant is combined with polyoxyethylene sorbitan monostearate and used to emulsify the liquid paraffin. Thus, the optimal proportion exhibiting stability is determined, and the HLB value of the unknown surfactant is represented by x, and x is substituted in foregoing expression (1) to determine x.

The lower limit of the content of the (C) component in the mixture of the first agent and the second agent is appropriately set, and is preferably 0.01% by mass or more, more preferably 0.05% by mass or more, and furthermore preferably 0.2% by mass or more. When the content of the (C) component is 0.01% by mass or more, a desired viscosity is achieved. The upper limit of the content of the (C) component in the mixture of the first agent and the second agent is appropriately set, and is preferably 10% by mass or less, more preferably 5% by mass or less, and furthermore preferably 3% by mass or less. When the content of the (C) component is 10% by mass or less, the stability of a formulation is more improved, and the miscibility at the time of use is more improved.

When a nonionic surfactant having a POE chain having a number of moles of added E.O. of 30 or more is used as the (C) component, the lower limit of the content of such a (C) component in the first agent is preferably 0.01% by mass or more, more preferably 0.05% by mass or more, and furthermore preferably 0.2% by mass or more. When the content of such a (C) component is 0.01% by mass or more, the stability of the first agent is more improved. The upper limit of the content of such a (C) component in the first agent is preferably 3% by mass or less, more preferably 2% by mass or less, and furthermore preferably 1.5% by mass or less. When the content of such a (C) component is 3% by mass or less, the miscibility at the time of use is more improved.

(D) The nonionic surfactant having an HLB value of 11 or less improves the miscibility at the time of use. Specific examples of the (D) component include POE(3) alkyl(C12 to 14) ether (HLB: 8), POE(2) cetyl ether (HLB: 8.0), POE(4) cetyl ether (HLB: 8.4), POE(5) cetyl ether (HLB: 9.5), POE(5.5) cetyl ether (HLB: 10.5), POE(1) polyoxypropylene(4) cetyl ether (HLB: 9.5), POE(10) polyoxypropylene(4) cetyl ether (HLB: 10.5), POE(12) polyoxypropylene(6) decyl tetradecyl ether (HLB: 8.5), POE(2) lauryl ether (HLB: 9.5), POE(3) lauryl ether (HLB: 8.4), POE(2) myristyl ether (HLB: 5.8), POE(3) myristyl ether (HLB: 7.7), POE(2) hexyl decyl ether (HLB: 5.3), POE(4) hexyl decyl ether (HLB: 8.4), POE(2) stearyl ether (HLB: 8.0), POE(4) stearyl ether (HLB: 9.0), POE(5) stearyl ether (HLB: 9.0), POE(2) oleyl ether (HLB: 4.9), POE(3) oleyl ether (HLB: 6.6), POE(2) octyl dodecyl ether (HLB: 4.6), POE(5) octyl dodecyl ether (HLB: 8.5), POE(2) behenyl ether (HLB: 4.3), POE(3) behenyl ether (HLB: 5.8), POE(5) behenyl ether (HLB: 7.0), POE(6) behenyl ether (HLB: 8.9), lipophilic glycerin monooleate (HLB: 2.5), lipophilic glycerin monostearate (HLB: 4.0), self-emulsifying glycerin monosterate (HLB: 6.0), sorbitan monooleate (HLB: 4.3), sorbitan sesquioleate (HLB: 3.7), sorbitan trioleate (HLB: 1.7), sorbitan monostearate (HLB: 4.7), sorbitan monopalmitate (HLB: 6.7), sorbitan monolaurate (HLB: 8.6), and sucrose fatty acid ester.

The lower limit of the content of the (D) component in the mixture of the first agent and the second agent is appropriately set, and is preferably 0.05% by mass or more, more preferably 0.1% by mass or more, and furthermore preferably 0.5% by mass or more. When the content of the (D) component is 0.05% by mass or more, the miscibility at the time of use is improved. The upper limit of the content of the (D) component in the mixture of the first agent and the second agent is appropriately set, and is preferably 10% by mass or less, more preferably 5% by mass or less, and furthermore preferably 3% by mass or less. When the content of the (D) component is 10% by mass or less, a desired viscosity is achieved.

The lower limit of the content of the (D) component in the first agent is appropriately set, and is preferably 0.1% by mass or more, more preferably 0.2% by mass or more, and furthermore preferably 1% by mass or more. When the content of the (D) component is 0.1% by mass or more, the miscibility at the time of use is improved. The upper limit of the content of the (D) component in the first agent is appropriately set, and is preferably 20% by mass or less, more preferably 10% by mass or less, and furthermore preferably 6% by mass or less. When the content of the (D) component is 20% by mass or less, a desired viscosity is achieved.

The lower limit of the mass ratio of the content of the (D) component to the content of the (C) component in the mixture of the first agent and the second agent is appropriately set, and is preferably 0.1 or more, more preferably 0.3 or more, and furthermore preferably 0.5 or more. When such a mass ratio is 0.1 or more, the miscibility at the time of use is more improved. The upper limit of the mass ratio of the content of the (D) component to the content of the (C) component in the mixture of the first agent and the second agent is appropriately set, and is preferably 2 or less, more preferably 1.7 or less, and furthermore preferably 1.5 or less. When such a mass ratio is 2 or less, a desired viscosity is achieved.

The lower limit of the mass ratio of the content of the (D) component to the content of the (C) component in the first agent is appropriately set, and is preferably 0.1 or more, more preferably 0.2 or more, and furthermore preferably 0.3 or more. When such a mass ratio is 0.1 or more, the miscibility at the time of use is more improved. The upper limit of the mass ratio of the content of the (D) component to the content of the (C) component in the first agent is appropriately set, and is preferably 2 or less, more preferably 1.7 or less, and furthermore preferably 1.5 or less. When such a mass ratio is 2 or less, a desired viscosity is achieved.

(E) A hydroxyalkyl cellulose or a derivative thereof more improves the miscibility between the first agent and the second agent at the time of use. Accordingly, the oxidative hair dye composition preferably contains the (E) component. From the viewpoint of more improving the miscibility between the first agent being a cream formulation and the second agent being liquid, the (E) component is more preferably mixed in the first agent. Specific examples of the (E) component include hydroxyethyl cellulose, hydroxypropyl cellulose, and hydroxypropyl methyl cellulose. Among these, from the viewpoint of being excellent in miscibility, hydroxyethyl cellulose is preferable.

The lower limit of the content of the (E) component in the mixture of the first agent and the second agent is appropriately set, and is preferably 0.01% by mass or more, more preferably 0.05% by mass or more, and furthermore preferably 0.1% by mass or more. When the content of the (E) component is 0.01% by mass or more, the miscibility between the first agent and the second agent at the time of use is more improved.

The upper limit of the content of the (E) component in the first agent and the second agent is appropriately set, and is preferably 10% by mass or less, more preferably 5% by mass or less, and furthermore preferably 2% by mass or less. When the content of the (E) component is 10% by mass or less, a desired viscosity is achieved.

The alkaline agent contained in the first agent acts to improve the hair dyeing effect by promoting the action of the oxidant contained in the second agent. Examples of the alkaline agent include ammonia, an alkanolamine, a silicate, a carbonate, a hydrogencarbonate, a metasilicate, a sulfate, a chloride, a phosphate, an organic amine, a basic amino acid, and a hydroxide of an alkali metal or an alkaline earth metal. Specific examples of the alkanolamine include monoethanolamine and triethanolamine. Specific examples of the silicate include sodium silicate and potassium silicate. Specific examples of the carbonate include sodium carbonate and ammonium carbonate. Specific examples of the hydrogencarbonate include sodium hydrogencarbonate and ammonium hydrogencarbonate. Specific examples of the metasilicate include sodium metasilicate and potassium metasilicate. Specific examples of the sulfate include ammonium sulfate. Specific examples of the chloride include ammonium chloride. Specific examples of the phosphate include ammonium dihydrogenphosphate and diammonium hydrogenphosphate. Specific examples of the organic amine include 2-amino-2-methyl-1-propanol (AMP), 2-amino-2-methyl-1,3-propanediol, and guanidine. Specific examples of the basic amino acid include arginine and lysine. Specific examples of the hydroxide of an alkali metal or an alkaline earth metal include sodium hydroxide and potassium hydroxide. Only one of these alkaline agents may be contained alone, or two or more of these alkaline agents may be contained in combination. Among these, from the viewpoint of improving the hair dyeing effect, ammonia, an ammonium salt, and an alkanolamine are preferably applied.

The content of the alkaline agent in the mixture of the first agent and the second agent is preferably such that the alkaline agent is mixed in such a way that the pH of the mixture falls within a range between 7 and 12. By regulating the pH of the mixture of the first agent and the second agent so as to be 7 or more, the action of the oxidant contained in the second agent is more promoted. By regulating the pH of the mixture of the first agent and the second agent so as to be 12 or less, the damage of hair due to the application of the oxidative hair dye composition is more suppressed.

The oxidative hair dye composition may further contain, if necessary, the components other than the foregoing components such as a solubilizer, a water-soluble polymer other than the foregoing water soluble polymers, an oily component, a polyhydric alcohol, a surfactant other than the foregoing surfactants, a pH adjuster, a sugar, a preservative, a stabilizer, a plant extract, a crude drug extract, a vitamin, a perfume, an antioxidant, a chelating agent, and an ultraviolet absorber.

A solubilizer makes the first agent into a cream formulation. Examples of the solubilizer used include water and an organic solvent. Specific examples of the organic solvent include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethyl phenethyl alcohol, α-phenylethanol, ethylene glycol phenyl ether (phenoxyethanol), phenoxyisopropanol, 2-benzyloxyethanol, an N-alkylpyrrolidone, an alkylene carbonate, and an alkyl ether. Only one of these solubilizers may be contained alone, or two or more of these solubilizers may be contained in combination. Among these, water is preferably applied because water is excellent in the capability of dissolving the other components in the first agent. When water is used as the solvent, the content of water in the mixture of the first agent and the second agent (the content at the time of use) is preferably 40% by mass or more and more preferably 50% by mass or more.

A water-soluble polymer imparts an appropriate viscosity to the oxidative hair dye composition. Accordingly, the oxidative hair dye composition may contain a water-soluble polymer within a range not impairing the advantageous effects of the present invention. Examples of the water-soluble polymer include a natural polymer, a semisynthetic polymer, a synthetic polymer, and an inorganic polymer. Specific examples of the natural polymer include guar gum, locust bean gum, quince seed, carrageenan, galactan, gum arabic, tragacanth gum, pectin, mannan, xanthan gum, dextran, succinoglucan, curdlan, hyaluronic acid, gelatin, casein, albumin, collagen, dextrin, and triglucopolysaccharide (pullulan).

Specific examples of the semisynthetic polymer include methyl cellulose, ethyl cellulose, carboxy methyl cellulose, sodium carboxy methyl cellulose, cationized cellulose, cationized guar gum, starch phosphate, propylene glycol alginate, and an alginic acid salt. Specific examples of the cationized cellulose include hydroxy ethyl cellulose dimethyl diallyl ammonium chloride.

Specific examples of the synthetic polymer include polyvinyl caprolactam, polyvinyl alcohol (PVA), polyvinylpyrrolidone (PVP), vinylpyrrolidone-vinyl acetate (VP/VA) copolymer, polyvinyl butylal, polyvinyl methyl ether, carboxyvinyl polymer, sodium polyacrylate, polyacrylamide, polyethylene oxide, ethylene oxide-propylene oxide block copolymer, acrylic acid/alkyl acrylate copolymer, polydimethylmethylene piperidinium chloride, and a copolymer composed of a semi-ester of itaconic acid and POE alkyl ether, or an ester of methacrylic acid and a POE alkyl ether, and at least one monomer selected from acrylic acid, methacrylic acid and alkyl esters of these acid. Only one of these water-soluble polymers may be contained alone, or two or more of these water-soluble polymers may be contained in combination.

The oily component imparts a moist feeling to hair. Accordingly, the oxidative hair dye composition may contain an oily component within a range not impairing the advantageous effects of the present invention. Examples of the oily component include an oil/fat, a wax, a higher alcohol, a hydrocarbon, a higher fatty acid, an alkyl glyceryl ether, an ester, and silicone.

Specific examples of the oil/fat include *Argania spinosa* kernel oil, lanolin, olive oil (purified olive oil), camellia oil, shea fat, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax include beeswax, candelilla wax, carnauba wax, jojoba oil, and lanolin wax. Specific examples of the higher alcohol include cetyl alcohol (cetanol), 2-hexyldecanol, stearyl alcohol, isostearyl alcohol, cetostearyl alcohol, oleyl alcohol, arachidyl alcohol, behenyl alcohol, 2-octyldodecanol, lauryl alcohol, myristyl alcohol, decyltetradecanol, and lanolin alcohol.

Specific examples of the hydrocarbon include paraffin, olefin oligomer, polyisobutene, hydrogenated polyisobutene, a mineral oil, squalane, polybutene, polyethylene, microcrystalline wax, and vaseline. Specific examples of the higher fatty acid include lauric acid, myristic acid, palmitic acid, stearic acid, behenic acid, isostearic acid, 12-hydroxy stearic acid, oleic acid, and lanolin fatty acid. Specific examples of the alkyl glyceryl ether include batyl alcohol, chimyl alcohol, selachyl alcohol, and isostearyl glyceryl ether.

Specific examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a fatty acid cholesteryl/lanosteryl ester having 10 to 30 carbon atoms, cetyl lactate, lanolin acetate, ethylene glycol di-2-ethylhexanoate, pentaerythritol fatty acid ester, dipentaerythritol fatty acid ester, cetyl caprate, glyceryl tricaprylate, diisostearyl malate, dioctyl succinate, cetyl 2-ethyl hexanoate, and hydrogenated castor oil isostearate.

Specific examples of the silicone include dimethylpolysiloxane (dimethicone), methylphenylpolysiloxane, decamethylcyclopentasiloxane, dodecamethylcyclohexasiloxane, a terminal hydroxyl group-modified dimethylpolysiloxane, a high polymerization silicone, a polyether-modified silicone (for example, (PEG/PPG/butylene/dimethicone) copolymer), an amino-modified silicone, a betaine-modified silicone, an alkyl-modified silicone, an alkoxy-modified silicone, a mercapto-modified silicone, a carboxy-modified silicone, and a fluorine-modified silicone. Only one of these oily components may be contained alone, or two or more of these oily components may be contained in combination.

Examples of the polyhydric alcohol include a glycol and glycerin. Examples of the glycol include ethylene glycol, diethylene glycol, triethylene glycol, polyethylene glycol, high-polymerization polyethylene glycol, propylene glycol, dipropylene glycol, polypropylene glycol, isoprene glycol, and 1,3-butylene glycol. Examples of the glycerin include glycerin, diglycerin, and polyglycerin. Only one of these polyhydric alcohols may be used alone, or two or more of these polyhydric alcohols may be used in combination.

The surfactant, as an emulsifying agent or a component for solubilizing the respective components, emulsifies or solubilizes the oxidative hair dye composition, and regulates the viscosity of the oxidative hair dye composition and improves the viscosity stability of the oxidative hair dye composition when the oxidative hair dye composition is used. Accordingly, the oxidative hair dye composition may contain a surfactant within a range not impairing the advantageous effects of the present invention. Examples of the surfactant include an anionic surfactant, an amphoteric surfactant, and a nonionic surfactant other than those described above.

Specific examples of the anionic surfactant include an alkyl ether sulfate, an alkyl sulfate, an alkyl ether sulfate ester salt, an alkenyl ether sulfate, an alkenyl sulfate, an olefin sulfonate, an alkane sulfonate, a saturated or unsaturated fatty acid salt, an alkyl or alkenyl ether carboxylate, an $\alpha$-sulfofatty acid salt, an N-acylamino acid-type surfactant, a phosphate mono- or di-ester-type surfactant, a sulfosuccinic acid ester, an N-alkyloylmethyl taurine salt, and a drivative thereof. Specific examples of the counterion of the anionic group of these surfactants include sodium ion, potassium ion, and triethanolamine.

Specific examples of the amphoteric surfactant include coco-betaine, lauramidopropyl betaine, cocamidopropyl betaine, sodium lauroamphoacetate, sodium cocoamphoacetate, coconut oil fatty acid amidopropyl betaine, lauryl betaine (betaine lauryldimethylamino acetate), and sodium laurylaminopropionate.

The nonionic surfactant is selected from nonionic surfactants each having an HLB value of more than 11 and less than 17 or from nonionic surfactant each having an HLB value of more than 20. Specific examples of the nonionic surfactant include an ether-type nonionic surfactant, an ester-type nonionic surfactant, and an alkyl glucoside. Specific examples of the ether-type nonionic surfactant include POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE polyoxypropylene cetyl ether, and POE polyoxypropylene decyl tetradecyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit beeswax, polyethylene glycol monooleate, polyethylene glycol monostearate, polyethylene glycol monolaurate, a sucrose fatty acid ester, decaglyceryl monolaurate, decaglyceryl monostearate, decaglyceryl monooleate, decaglyceryl monomyristate.

Specific examples of the alkyl glucoside include an alkyl (having 8 to 16 carbon atoms) glucoside, POE methyl glucoside, and POE methyl glucoside dioleate. Only one of these specific examples of the surfactant may be contained alone, or two or more of these specific examples of the surfactant may be contained in combination.

The pH adjuster may be mixed in order to adjust the pH of the oxidative hair dye composition. The pH adjuster may be selected from the known pH adjusters. Examples of the pH adjuster include an inorganic acid, an organic acid, and a salt thereof. Specific examples of the organic acid include citric acid, glycolic acid, succinic acid, tartaric acid, lactic acid, malic acid, levulinic acid, acetic acid, butyric acid, valeric acid, oxalic acid, maleic acid, fumaric acid, and mandelic acid. Specific examples of the organic acid salt include a sodium salt, a potassium salt, and an ammonium salt. Specific examples of the inorganic acid include phosphoric acids such as phosphoric acid and pyrophosphoric acid, hydrochloric acid, sulfuric acid, and nitric acid. These may be used each alone, or in combinations of two or more thereof.

Specific example of the sugar include: monosaccharides such as glucose and galactose; disaccharides such as maltose, sucrose, fructose, and trehalose; and a sugar alcohol. Specific examples of the preservative include paraben, methylparaben, and sodium benzoate. Specific examples of the stabilizer include phenacetin, 8-hydroxyquinoline, acetanilide, sodium pyrophosphate, barbituric acid, uric acid, and tannic acid. Specific examples of the antioxidant include ascorbic acids and sulfites. Specific examples of the chelating agent include edetic acid (ethylenediaminetetraacetic acid (EDTA)), disodium edetate, tetrasodium edetate, diethylenetriaminepentaacetic acid and salts thereof, ethylenediaminehydroxyethyl triacetic acid and salts thereof, and hydroxyethane diphosphonic acid (HEDP) and salts thereof.

The formulation of the first agent is in a cream state at 25° C. Accordingly, the stability of the first agent is improved. In addition, a desired viscosity is imparted to the mixture with the second agent, which in a liquid state.

(Second Agent of Two-Part Type Oxidative Hair Dye Composition)

The second agent contains the foregoing solubilizer and the like in addition to the oxidant. The oxidant more improves the decolorization property for melanin contained in hair. Specific examples of the oxidant include hydrogen peroxide, urea peroxide, melamine peroxide, sodium percarbonate, potassium percarbonate, sodium perborate, potassium perborate, ammonium persulfate, potassium persulfate, sodium persulfate, sodium peroxide, potassium peroxide, magnesium peroxide, barium peroxide, calcium peroxide, strontium peroxide, hydrogen peroxide adducts of sulfates, hydrogen peroxide adducts of phosphates, and hydrogen peroxide adducts of pyrophosphates. Only one of these specific examples of the oxidant may be contained alone, or two or more of these specific examples may be contained in combination. The content of the oxidant in the second agent is appropriately set, and is preferably 0.1% by mass or more, more preferably 2% by mass or more, and furthermore preferably 3% by mass or more. When the content of the oxidant is 0.1% by mass or more, the decolorization property for melanin is more improved. The content of the oxidant in the second agent is preferably 15% by mass or less, more preferably 9% by mass or less, and furthermore preferably 6% by mass or less. When the content of the oxidant is 15% by mass or less, the damage of hair and the like can be more suppressed.

When hydrogen peroxide is mixed in the second agent as an oxidant, for the purpose of improving the stability of hydrogen peroxide, the second agent preferably contains a stabilizer such as sodium stannate, ethylene glycol phenyl ether (phenoxyethanol), hydroxyethane diphosphonic acid and a salt thereof. Examples of the hydroxyethane diphosphonic acid salt include tetrasodium hydroxyethane diphosphonate and disodium hydroxyethane diphosphonate. The second agent may contain the components that are generally contained in an oxidative hair dye composition and that do not disturbing the actions of the foregoing respective components. For example, the second agent may optionally contain the foregoing components contained in the first agent within the ranges not impairing the advantageous effects of the present invention.

The second agent is a liquid formulation such as an aqueous solution or an emulsion at 25° C. A liquid state such as an emulsion state is preferable from the viewpoint of the improvement of the miscibility with the first agent, which is a cream formulation.

<Three-or-More-Part Type Oxidative Hair Dye Composition>

For example, the first agent of a two-part type oxidative hair dye composition may be divided into an agent containing the alkaline agent and an agent containing the components other than the alkaline agent, to thereby constitute a three-part type oxidative hair dye composition. In this case, the three-part type oxidative hair dye composition has satisfactory formulation stability. In this way, from the viewpoint of the formulation stability and the like, the respective components contained in the first agent or the second agent may be stored as divided into a plurality of agents. Even when the oxidative hair dye composition is constituted as a three or more part type, such an oxidative hair dye composition is still included in the present invention as long as the advantageous effects of the present invention are achieved.

<Preparation of Oxidative Hair Dye Composition Mixture>

In the oxidative hair dye composition, the foregoing respective agents are mixed with each other at the time of use, and thus a mixture is prepared when the oxidative hair dye composition is used. In the preparation of the mixture, the mixture may be prepared by placing predetermined amounts of the respective agents in an airtight container having a predetermined volume and by shaking and mixing the respective agents together. Alternatively, the mixture may also be prepared by placing the respective agents in a vessel such as a tray and by stirring and mixing the respective agents together with a brush, a stirring rod, or the like. Mixing by shaking by using a tubular airtight container having a volume of 100 to 300 mL is preferable from the viewpoint of easy mixing operation. The total volume of the mixture in the container is preferably 20 to 80% by volume relative to the internal volume of the airtight container from the viewpoint of improving the miscibility. The shaking-mixing with an airtight container containing the respective agents placed therein may be performed by manual up-and-down/right-and-left reciprocating motion, or may be performed mechanically by using a vibration exciter or the like. The obtained mixture of the oxidative hair dye composition is applied to hair in a just necessary amount by using, for example, hands with thin gloves, a comb, or a brush, or a container with a lid having a discharge opening or with a comb.

The viscosity of the mixture at the time of use is 3,000 to 10,000 millipascal (mPa·s) at 25° C., and is preferably 4,000 to 9,000 mPa·s at 25° C. In particular, when the mixture is applied to hair by using a container with a lid or a comb having a discharge flow path or a discharge opening of 1.2 to 2.5 mm in internal diameter, the discharge property from the discharge opening and the application property is improved. The viscosity can be determined by using, for example, a B-type viscometer under the measurement conditions of 25° C. and 1 minute. Specific examples of the B-type viscometer include a BL-type viscometer (manufactured by Toki Sangyo Co., Ltd.). The rotor used and the rotation speed are appropriately selected according to the measurable viscosity range of the measurement apparatus. For example, a viscosity can be determined by using a size 3 rotor under the condition of 120 rpm. The viscosity of the mixture can be appropriately regulated by varying the mixing proportions of, for example, the foregoing solubilizer, water-soluble polymer, oily component and surfactant.

The oxidative hair dye composition according to the present embodiment has the following advantages.

(1) The oxidative hair dye composition according to the present embodiment is composed of a plurality of agents, and uses an oxidative dye that is an acid addition salt, wherein (B) a cationic surfactant in a content of 0.15% by mass or more, (C) a nonionic surfactant having an HLB value of 17 to 20, and (D) a nonionic surfactant having an HLB value of 11 or less are used in combination. Accordingly, a desired viscosity is imparted to the mixture. In addition, the miscibility between the first agent, which is a cream formulation, and the second agent, which is in a liquid state, is improved at the time of use.

(2) In the oxidative hair dye composition according to the present embodiment, the viscosity at 25° C. is 3,000 to 10,000 mPa·s. Accordingly, dripping or the like does not occur, and the oxidative hair dye composition has a satisfactory application property. In particular, when the mixture is applied to hair by using a container with a lid or a comb having a discharge flow path or a discharge opening of 1.2 to 2.5 mm in internal diameter, the discharge property from the discharge opening and the application property are improved.

The above-described embodiment may be modified as follows.

The oxidative hair dye composition of the above-described embodiment achieves advantageous effects of the present invention when the (A) to (D) components are contained in the mixture at the time of use. Accordingly, when the oxidative hair dye composition is constituted as a two or more part type formulation, the (A) to (D) components may be contained in any of the agents during storage.

In the above-described embodiment, some of the components contained in the first agent, the second agent, or the third agent of the oxidative hair dye composition may constitute an additional agent to increase the number of the agents constituting the oxidative hair dye composition.

The viscosity range of the first agent or the second agent is not particularly limited; however, in the case of an emulsion formulation, the viscosity at 25° C. is preferably 3,000 to 10,000 millipascal second (mPa·s). In the case of a cream or gel formulation, the viscosity at 25° C. is preferably 10,000 to 50,000 mPa·s. A viscosity can be measured by using, for example, a B-type viscometer by the same method as described above.

In the embodiment, a direct dye listed in, for example, "The Japanese Standards of Quasi-Drug Ingredients" (published by Yakuji Nippo Ltd., June 2006) may be optionally contained as a dye other than the foregoing oxidative dye, within a range not impairing the advantageous effects of the present invention.

EXAMPLES

Next, the foregoing embodiments will be described more specifically with reference to Examples and Comparative Examples. The present invention is not limited to the constitutions described in the Examples section.

As oxidative hair dye compositions, first agents that were cream formulations containing the components shown in Tables 1 to 3 and second agents that were emulsion formulations were prepared. It is to be noted that the numerical values in the rows of the respective components in the respective tables show the contents of the components concerned and the units thereof are percent by mass. The symbols (A) to (E) in the "Components" columns in the tables represent the compounds corresponding to the respective components described in the claims of the present application. The symbol "c" in the "Components" column in the table represents a compound for comparison with the component described in the claim of the present application.

The viscosity of each of the first agents prepared as described above was measured. The viscosity can be determined by using, as a B-type viscometer, a BL-type viscometer (manufactured by Toki Sangyo Co., Ltd.) and a size 3 rotor under the conditions of 120 rpm and 25° C. The formulation stability of the first agent was evaluated by the following method.

Next, in each of Examples and Comparative Examples, the first agent of the oxidative hair dye composition shown in Table 1 or 2, and the second agent of the oxidative hair dye composition shown in Table 3 were mixed with each other in a ratio of 2:3 to prepare a mixture of the oxidative hair dye composition. The mixing operation of the first agent and the second agent was performed by using a cylindrical airtight lidded container (internal volume: 200 mL) of 12 cm in height and 4.5 cm in diameter; the first agent and the second agent were charged in a total volume shown in Table 1 or 2. Then the container was shaken in an up-down direction 30 times as reciprocating motion, and thus, the first agent and the second agent were mixed with each other. The viscosity of the obtained mixture was measured under the same conditions as described above. The miscibility in the mixing of the first agent and the second agent was evaluated by the following method.

(Formulation Stability of First Agent)

The first agent of each of Examples and Comparative Examples was placed in a glass bottle, and stored in a thermostatic chamber at 60° C. for 24 hours; then the separation state of the first agent was visually evaluated, and thus it was determined whether or not the retention effect of the first agent, which was in a cream state, was satisfactory. The case where no separation was observed was evaluated as 5, the case where a slight separation was observed was evaluated as 3, the case where a considerable separation was observed was evaluated as 1; the cases corresponding to the intermediates of these three cases were evaluated as 4 and 2, respectively. The results thus obtained are shown in the tables presented below.

(Miscibility)

Five panelists charged airtight lidded containers with the first agent and the second agent, shook the containers gently 10 times in the up-down direction, then visually evaluated the state of the mixture, namely, the mixing degree after the shaking on the basis of the following standards, and thus determined the miscibility. The miscibility of the mixture was scored on the basis of the following 5-point scale: the case where any nonuniform portion was absolutely absent was evaluated as 5, the case where nonuniform portions were nearly absent was evaluated as 4, the case where nonuniform portions slightly remained was evaluated as 3, the case where nonuniform portions were easily found to remain was evaluated as 2, and the case where nonuniform portions remained to a large extent was evaluated as 1. The scoring results of the panelists were averaged. The mixture was rated as "excellent: 5", "good: 4", "fair: 3", "slightly poor: 2", or "poor: 1" when the average score was 4.6 points or more, 3.6 points or more and less than 4.6 points, 2.6 points or more and less than 3.6 points, 1.6 points or more and less than 2.6 points, or less than 1.6 points, respectively. The results thus obtained are shown in the tables presented below.

(Evaluation of Viscosity Value of Mixture)

The mixture obtained by mixing the first agent and the second agent with each other was evaluated as follows. The case where the viscosity of the mixture was 4,000 to 6,000 mPa·s was evaluated as 5. The case where the viscosity of the mixture was 3,500 mPa·s or more and less than 4,000 mPa·s and the case where the viscosity was more than 6,000 mPa·s and 8,000 mPa·s or less were evaluated as 4. The case where the viscosity of the mixture was 3,000 mPa·s or more and less than 3,500 mPa·s and the case where the viscosity was more than 8,000 mPa·s and 10,000 mPa·s or less were evaluated as 3. The case where the viscosity of the mixture was 2,500 mPa·s or more and less than 3,000 mPa·s and the case where the viscosity was more than 10,000 mPa·s and 12,000 mPa·s or less were evaluated as 2. The case where the viscosity of the mixture was less than 2,500 mPa·s or more than 12,000 mPa·s was evaluated as 1. The results thus obtained are shown in the tables presented below.

TABLE 1

| | Components of first agent | Example 1 | Example 2 | Example 3 | Example 4 | Example 5 | Example 6 |
|---|---|---|---|---|---|---|---|
| (A) | p-Toluylenediamine sulfate | 3.5 | 3.5 | 3.5 | 3.5 | 3.5 | 3.5 |
| | Resorcin | 0.5 | 0.5 | 0.5 | 0.5 | 0.5 | 0.5 |
| | m-Aminophenol | 0.2 | 0.2 | 0.2 | 0.2 | 0.2 | 0.2 |
| | 1-Naphthol | 0.2 | 0.2 | 0.2 | 0.2 | 0.2 | 0.2 |
| (B) | Behenyl trimethyl ammonium chloride (number of carbon atoms: 22) | 1 | — | 1 | 1 | 1 | 1 |
| (B) | Stearyl trimethyl ammonium chloride (number of carbon atoms: 18) | — | 1 | — | — | — | — |
| (C) | POE(50) oleyl ether (HLB: 18) | 1 | 1 | 2 | — | 0.7 | 1 |
| (C) | POE(20) cetyl ether (HLB: 17) | 2 | 2 | 4 | 3 | 1.3 | 2 |
| (D) | POE(2) stearyl ether (HLB: 8.0) | 2.5 | 2.5 | 2.5 | 2.5 | 3.5 | 2.5 |
| | Behenyl alcohol | 0.5 | 0.5 | 0.5 | 0.5 | 0.5 | 0.5 |
| | Stearyl alcohol | 7 | 7 | 7 | 7 | 7 | 7 |
| | 2-Octyldodecanol | 1 | 1 | 1 | 1 | 1 | 1 |
| (E) | Hydroxyethyl cellulose | 0.5 | 0.5 | 0.5 | 0.5 | 0.5 | — |
| | Polyethylene glycol (number average molecular weight: 400) | 7 | 7 | 7 | 7 | 7 | 7 |
| | Vaseline | 1 | 1 | 1 | 1 | 1 | 1 |
| | Polydimethylmethylene piperidinium chloride solution (40% by mass) | 1 | 1 | 1 | 1 | 1 | 2.2 |
| | L-Ascorbic acid | 0.3 | 0.3 | 0.3 | 0.3 | 0.3 | 0.3 |
| | Trisodium hydroxyethyl ethylenediamine triacetate solution (40% by mass) | 0.5 | 0.5 | 0.5 | 0.5 | 0.5 | 0.5 |
| | Anhydrous sodium sulfite | 0.2 | 0.2 | 0.2 | 0.2 | 0.2 | 0.2 |
| | 28% by mass Ammonia water | 1 | 1 | 1 | 1 | 1 | 1 |
| | 70% by mass Monoethanolamine | 6 | 6 | 6 | 6 | 6 | 6 |
| | Purified water | Balance | Balance | Balance | Balance | Balance | Balance |
| | Total | 100 | 100 | 100 | 100 | 100 | 100 |
| | Filling ratio (% by volume) of mixture in container | 60% | 60% | 60% | 60% | 60% | 60% |
| | Viscosity of mixture (mPa · s) | 4,590 | 3,430 | 5,340 | 3,550 | 3,060 | 5,590 |
| | Content of B component in mixture | 0.52 | 0.52 | 0.52 | 0.52 | 0.52 | 0.52 |
| | Content of D component/content of C component | 0.83 | 0.83 | 0.42 | 0.83 | 1.75 | 0.83 |
| Evaluations | | | | | | | |
| | Miscibility | 5 | 4 | 3 | 5 | 5 | 3 |
| | Formulation stability of first agent | 5 | 5 | 5 | 4 | 5 | 5 |
| | Evaluation of viscosity value | 5 | 3 | 5 | 4 | 3 | 5 |

TABLE 2

| | Components of first agent | Example 7 | Example 8 | Comparative Example 1 | Comparative Example 2 | Comparative Example 3 |
|---|---|---|---|---|---|---|
| (A) | p-Toluylenediamine sulfate | 3.5 | 3.5 | 3.5 | 3.5 | 3.5 |
| | Resorcin | 0.5 | 0.5 | 0.5 | 0.5 | 0.5 |
| | m-Aminophenol | 0.2 | 0.2 | 0.2 | 0.2 | 0.2 |
| | 1-Naphthol | 0.2 | 0.2 | 0.2 | 0.2 | 0.2 |
| (B) | Behenyl trimethyl ammonium chloride (number of carbon atoms: 22) | 1 | 1 | — | 1 | 1 |
| (C) | POE(50) oleyl ether (HLB: 18) | 1 | 1 | 1 | — | 1 |
| (C) | POE(20) cetyl ether (HLB: 17) | 2 | 2 | 2.8 | — | 4.5 |
| c | POE(10) cetyl ether (HLB: 13.5) | — | — | — | 3 | — |

TABLE 2-continued

| Components of first agent | Example 7 | Example 8 | Comparative Example 1 | Comparative Example 2 | Comparative Example 3 |
|---|---|---|---|---|---|
| (D) POE(2) stearyl ether (HLB: 8.0) | 2.5 | 2.5 | 2.5 | 2.5 | — |
| Behenyl alcohol | 0.5 | 0.5 | 0.5 | 0.5 | 0.5 |
| Stearyl alcohol | 7 | 7 | 7 | 7 | 7 |
| 2-Octyldodecanol | 1 | 1 | 1 | 1 | 1 |
| (E) Hydroxyethyl cellulose | 0.5 | 0.5 | 0.5 | 0.5 | 0.5 |
| Polyethylene glycol (number average molecular weight: 400) | 7 | 7 | 7 | 7 | 7 |
| Vaseline | 1 | 1 | 1 | 1 | 1 |
| Polydimethylmethylene piperidinium chloride solution (40% by mass) | 1 | 1 | 1 | 1 | 1 |
| L-Ascorbic acid | 0.3 | 0.3 | 0.3 | 0.3 | 0.3 |
| Trisodium hydroxyethyl ethylenediamine triacetate solution (40% by mass) | 0.5 | 0.5 | 0.5 | 0.5 | 0.5 |
| Anhydrous sodium sulfite | 0.2 | 0.2 | 0.2 | 0.2 | 0.2 |
| 28% by mass Ammonia water | 1 | 1 | 1 | 1 | 1 |
| 70% by mass Monoethanolamine | 6 | 6 | 6 | 6 | 6 |
| Purified water | Balance | Balance | Balance | Balance | Balance |
| Total | 100 | 100 | 100 | 100 | 100 |
| Filling ratio (% by volume) of mixture in container | 20% | 80% | 60% | 60% | 60% |
| Viscosity of mixture (mPas) | — | — | 2,050 | 1,600 | 4,590 |
| Content of B component in mixture | 0.52 | 0.52 | 0.12 | 0.52 | 0.52 |
| Content of D component/content of C component | 0.83 | 0.83 | 0.66 | — | — |
| Evaluations | | | | | |
| Miscibility | 3 | 3 | 5 | 5 | 1 |
| Formulation stability of first agent | 5 | 5 | 1 | 5 | 5 |
| Evaluation of viscosity value | — | — | 1 | 1 | 5 |

TABLE 3

| Components of second agent (emulsion formulation) | |
|---|---|
| 35% by mass Hydrogen peroxide | 15 |
| Cetanol | 1 |
| POE(10) cetyl ether (HLB: 13.5) | 0.2 |
| (B) Stearyl trimethyl ammonium chloride | 0.2 |
| Hydroxyethane diphosphonic acid | 0.05 |
| Tetrasodium hydroxyethane diphosphonate | 0.05 |
| Purified water | Balance |
| Total | 100 |

As shown in Tables 1 and 2, each of Examples was determined to have the results that each of the evaluation items was rated as 3 or higher. As shown in Example 7, when the filling ratio of the mixture in the container was 20% by volume, the contact force of the liquid mixture against the internal wall was weak during the mixing operation, and consequently the evaluation of the miscibility was poorer than Example 1 (filling ratio: 60% by volume). On the other hand, when the filling ratio of the mixture in the container was 80% by volume, the air dispersibility in the liquid mixture was weak during the mixing operation, and consequently the evaluation of the miscibility was poorer than Example 1 (filling ratio: 60% by volume).

As shown in Table 2, Comparative Example 1 having a low content of the (B) component was determined to be poorer in the evaluations of the formulation stability of the first agent and the viscosity value of the mixture than any Examples. Comparative Example 2 using a nonionic surfactant having an HLB value of 13.5 in place of the (C) component was determined to be poorer in the evaluation of the viscosity value of the mixture than any Examples.

Comparative Example 3 not containing the (D) component was determined to be poorer in the evaluation of the miscibility than any Examples.

The foregoing embodiment and Examples are presented as exemplification for describing the present invention, and the present invention is not limited to the foregoing embodiment and Examples. For the embodiment disclosed for exemplification, various alternatives, alterations and modifications can be made without departing from the gist and scope of the present invention. For example, the subject of the present invention may possibly reside in features smaller in number than all the features of the particular disclosed embodiment. Accordingly, the scope of the claims of the invention is incorporated into the detailed description, and each of the claims itself claims a separate embodiment. The scope of the present invention is intended to include, in the scope of the claims, all of such alternative forms, alteration forms and modification forms, together with all the equivalents of these forms.

The invention claimed is:

1. An oxidative hair dye composition comprising a first agent that includes an alkaline agent and is a cream formulation and a second agent that includes an oxidant and is liquid, and the oxidative hair dye composition at the time of use having a viscosity at 25° C. of 3,000 to 10,000 mPa·s, wherein the oxidative hair dye composition further comprises:
   (A) a salt of an oxidative dye;
   (B) a cationic surfactant in a content of 0.15% by mass or more;
   two or more nonionic surfactants comprising (C) a nonionic surfactant having an HLB value of 17 to 20 and
   (D) a nonionic surfactant having an HLB value of 11 or less, the mass ratio of the content of the (D) component to the content of the (C) component is 0.1 to 2; and (E) a hydroxyalkyl cellulose selected from the group consisting of hydroxyethyl cellulose, hydroxypropyl cellulose, and hydroxypropyl methyl cellulose.

2. The oxidative hair dye composition according to claim 1, wherein the (B) component has an alkyl group having 20 or more carbon atoms.

3. The oxidative hair dye composition according to claim 1, wherein the first agent and the second agent are shaken and mixed with each other in an airtight container at the time of use; and a filling ratio of the mixture of the first agent and the second agent in the airtight container is 20 to 80% by volume.

4. The oxidative hair dye composition according to claim 1, wherein the two or more nonionic surfactants consist of one or more (C) components and one or more (D) components, the content of the one or more (C) components in a mixture of the first agent and the second agent is 5% by mass or less, and the content of the one or more (D) components in a mixture of the first agent and the second agent is 5% by mass or less.

5. The oxidative hair dye composition according to claim 1, wherein the two or more nonionic surfactants are contained in the first agent and consist of one or more (C) components and one or more (D) components, the content of the one or more (C) components in the first agent is 6% by mass or less, and the content of the one or more (D) components in the first agent is 6% by mass or less.

\* \* \* \* \*